US00PP10556P

United States Patent [19]

Bjorge et al.

[11] Patent Number: Plant 10,556

[45] Date of Patent: Aug. 18, 1998

[54] 'FA 17' PEACH TREE

[75] Inventors: Annette Bjorge; Randy Bjorge, both of Coloma, Mich.

[73] Assignee: International Plant Management, Lawrence, Mich.

[21] Appl. No.: 738,253

[22] Filed: Oct. 28, 1996

[51] Int. Cl.[6] ..... A01H 5/00

[52] U.S. Cl. ..... Plt./43.2

[58] Field of Search ..... Plt./43.2

[56] References Cited

U.S. PATENT DOCUMENTS

P.P. 9,939 7/1997 Friday ..... Plt./43.2

*Primary Examiner*—James R. Feyrer

[57] ABSTRACT

A new peach variety, *Prunus persica*, (hereinafter referred to as the FA 17 peach tree variety) which was developed by Annette and Randy Bjorge in a breeding program at Fruit Acres Farm in Coloma, Mich., having the following combination of unique and desirable features:

1. A fruit with excellent shipping and storage qualities.
2. A fruit maturing 30 days later than the 'Redhaven' peach.
3. A substantially round peach with clear yellow flesh and an attractive dark red blush over a brilliant orange background covering about 80 to 90% of the fruit at maturity.
4. A fruit and tree with good resistance to Bacterial Spot.
5. A fruit with flesh that does not brown when cut.
6. A fruit and tree with exceptional hardiness.

3 Drawing Sheets

ORIGIN OF THE VARIETY

The new variety of peach tree 'FA 17' was developed by Annette and Randy Bjorge in a peach breeding program at Fruit Acres Farms, 2559 Friday Road, Coloma, Mi. 49038. The 'FA 17' peach tree was developed as a first generation cross between 'Fayette' and 'Newhaven', two established, non-patented, commercial varieties. The parent tree was grown and maintained in a peach tree breeding orchard in Fruit Acres Farms.

This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of upright, vigorous growth with medium density and is a regular and very productive bearer of peaches. The fruit of the new variety is characterized by round, substantially 80 to 90% rich dark red over bright orange fruits with a blush color pattern and some soft, indistinct striping that presents a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The new variety is a very heavy, consistent producer. The tree and fruits of the new variety exhibit good resistance to Bacterial Spot and are very cold hardy. The fruit matures at the end of the peach growing season in Southwestern Michigan. It ripens 30 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

FIG. 1. illustrates specimens of the fully ripened fruit and foliage of the new variety.

FIG. 2. illustrates blooms of the new variety.

FIG. 3. Illustrates two specimens of the new variety. The upper specimen is bisected along the suture, the lower specimen is bisected as a ninety-degree angle to the plane of the suture. The color and forms of the flesh, pit and pit cavity are illustrated.

DETAILED DESCRIPTION OF THE VARIETY

Figure 1:
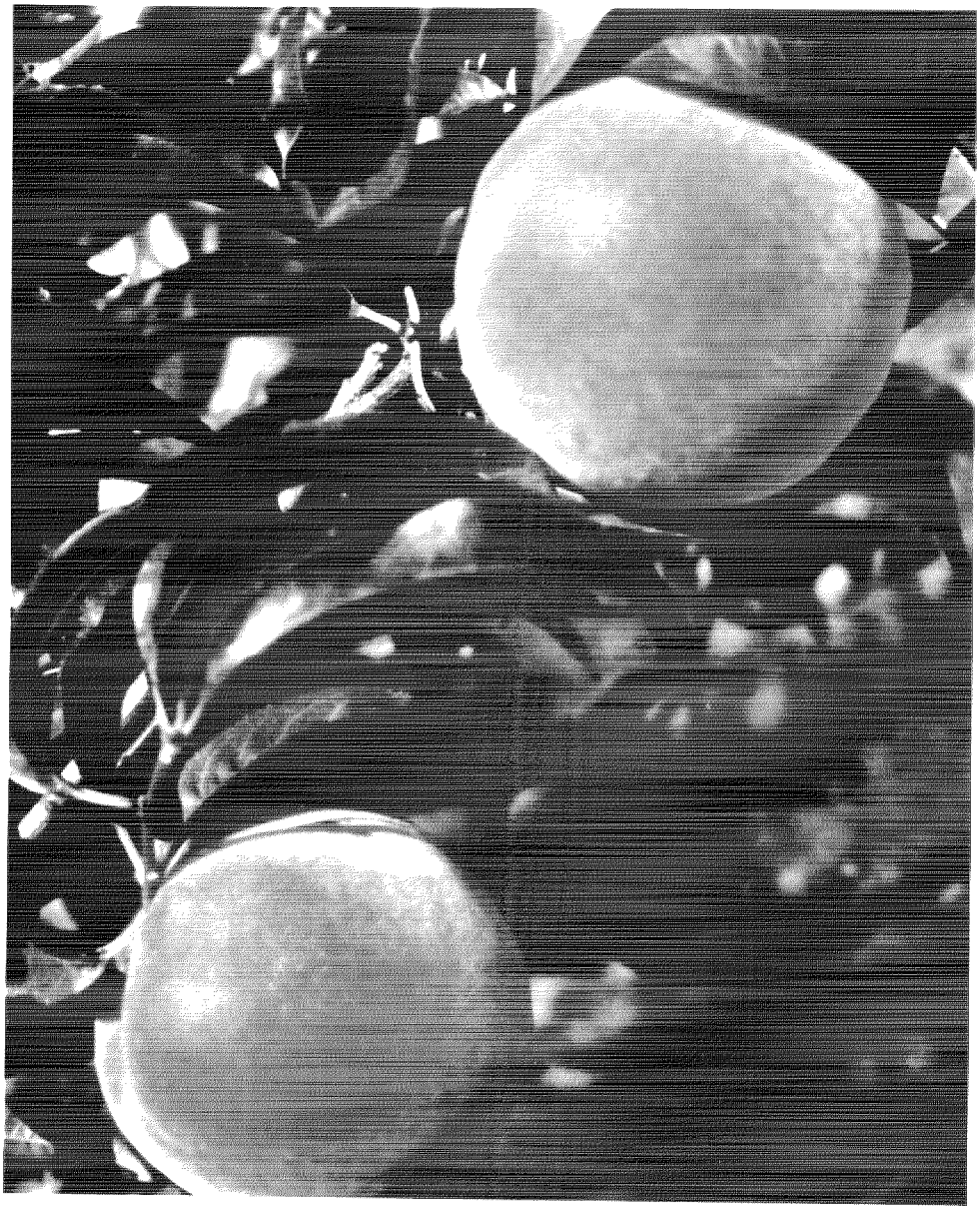
Figure 2:
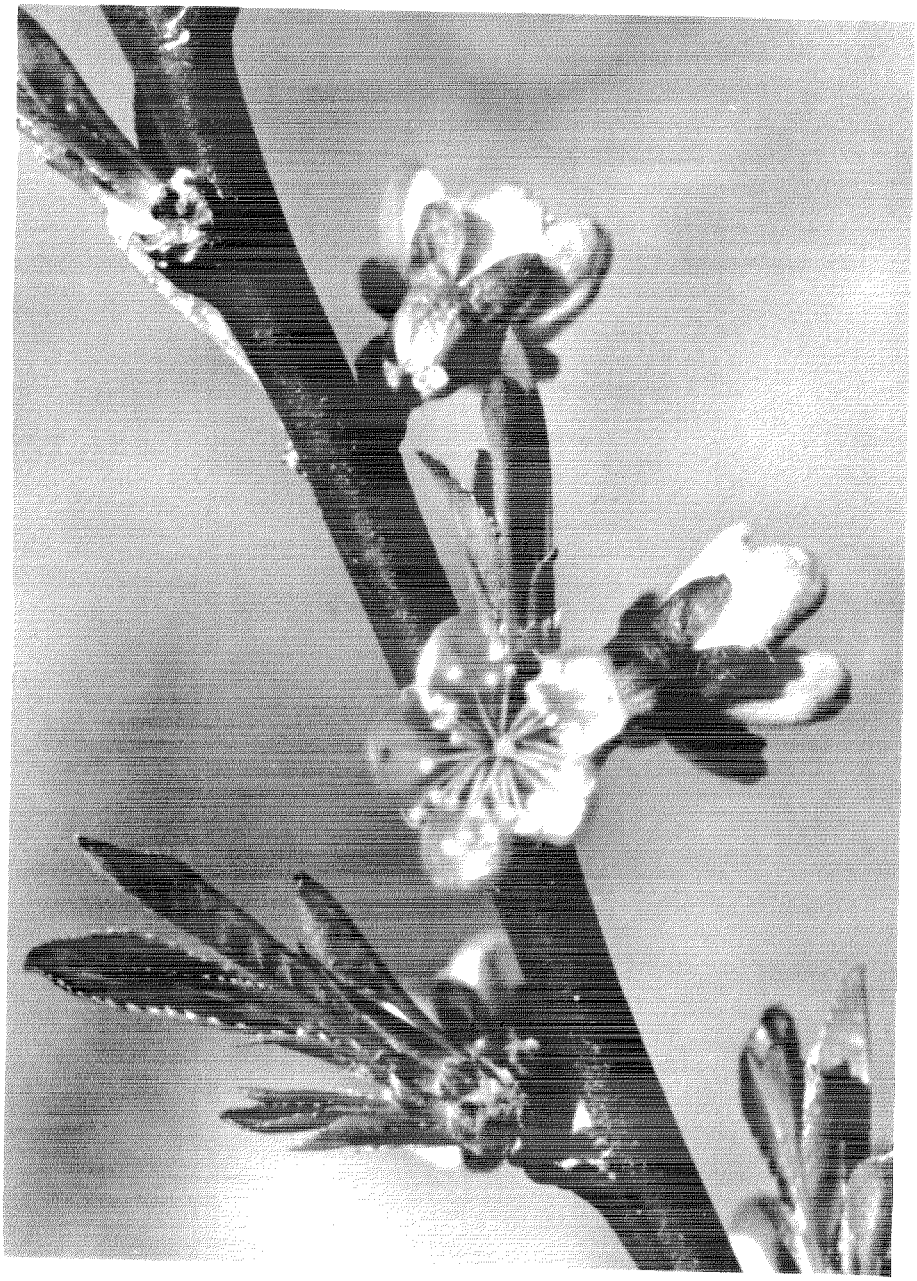
Figure 3:
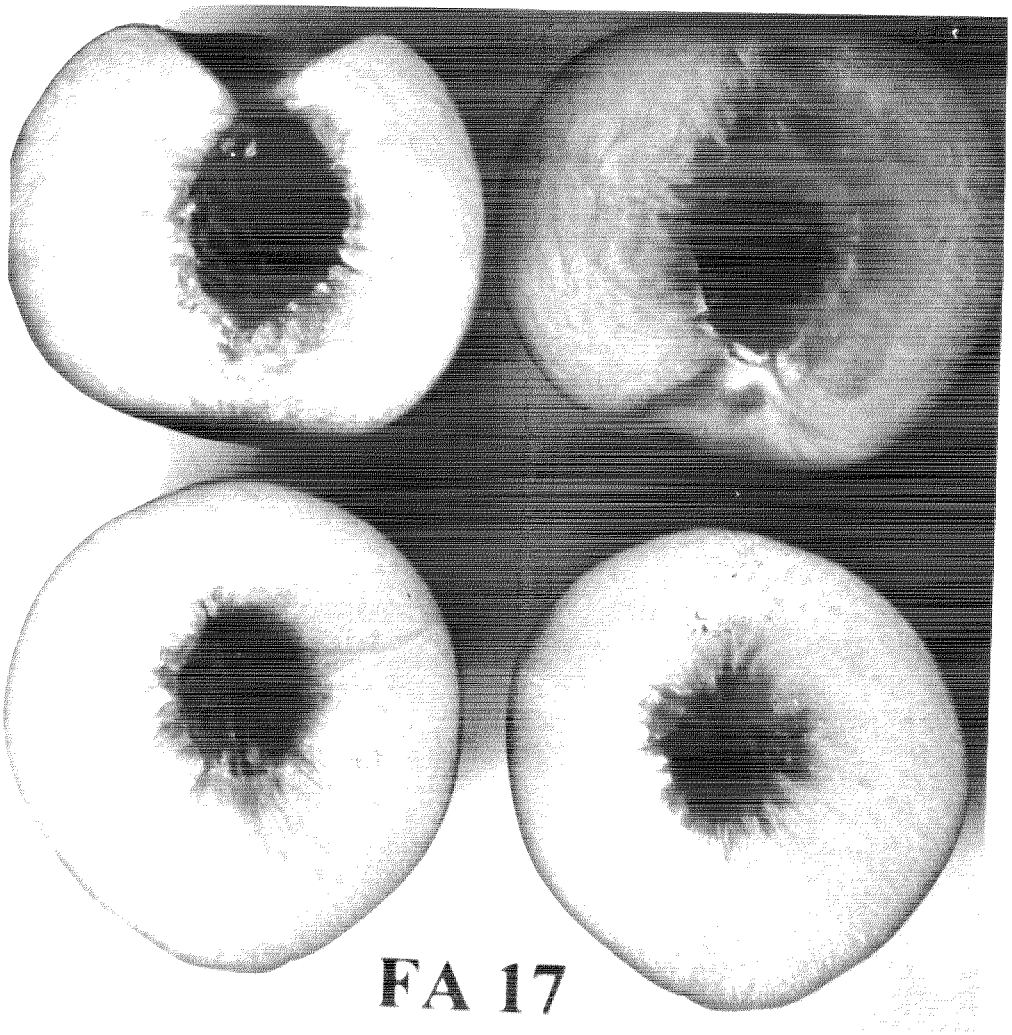

The following description of the fruit and foliage of the new variety is based on observations of specimens grown in Berrien and Van Buren County of Southwestern Michigan. The color terminology is in accordance with The Royal Horticultural Society Colour Chart, published by The Royal Horticultural Society of London, England.

Tree:

*Age of the specimen.*—15 years.

*Height.*—Unpruned 4.6 M.

*Width.*—Unpruned 5 M.

*Size.*—Medium.

*Vigor.*—High, requires moderate thinning and spring pruning.

*Density.*—medium. Internode length averages 1½ to 2 cm.

*Form.*—Open. Major scaffold branches form 45° angles tot he trunk. Tree will form a central leader if left unpruned. It does not require supplemental support.

*Production.*—Very productive, uniform ripening. Ripens in 1 to 2 pickings with 80% of the crop reaching maturity for the first picking. It is more productive that its parents and similar in productivity to Redhaven.

*Bearing.*—Annual. Harvest season averages 3 days.

*Disease resistance.*—good resistance to bacterial spot.

*Cold hardiness.*—Very hardy.

Trunk:

*Size.*—Medium.

*Surface.*—Smooth.
*Lenticils.*—Small.
*Color.*—Gray 201 B.

Leaves:
*Size.*—Length 138 mm, width 36 mm.
*Form.*—Lanceolate, pointed.
*Thickness.*—Medium.
*Texture.*—Medium.
*Margin.*—Serrate.
*Petiole.*—Length 13 mm , straight, medium thickness.
*Glands.*—Round, number varies from 3 to 5, average 5. Located on base of leaf and upper portion of petiole.
*Color.*—Upper surface green 147 A, lower surface green 147 B.
*Stipules.*—None.

Flower buds:
*Size.*—Medium.
*Length.*—Medium.

Flowers:
*Blooming period.*—April 8 to 15 in Coloma, Mich.
*Presentation.*—Medium showy.
*Pollen.*—Present, self fertilizing.
*Petals.*—5 in number, 15 mm long, 11mm wide. Red-purple 73A.
*Stamens.*—Slightly curved inward, 10–12 mm long.
*Pistil.*—15–17 mm long, white 155 A.

Fruit:
*Maturity when described.*—Firm ripe.
*Date of first picking.*—September 6th in Southwestern Michigan, 30 days after 'Redhaven'.
*Size.*—65 to 80 mm.
*Form.*—Round.
*Suture.*—Indistinct, clean.
*Pistil point.*—Recessed.
*Blossom end.*—Recessed, picks dry without tearing.

Skin:
*Thickness.*—Thin.
*Texture.*—Fine.
*Tendency to crack.*—None.
*Down.*—Moderate.
*Color.*—Beautiful, dark 80 to 90% red 46 A blush with some indistinct soft striping, red 44 B, over a background of yellow-orange 20 B.

Flesh:
*Texture.*—Fine, firm.
*Aroma.*—Distinct, medium pungency.
*Fibres.*—Few, small, tender, not conspicuous or noticeable in eating.
*Color.*—Yellow-orange 20 C.
*Coloration at the pit.*—Bright pinkish-red bleeding into flesh around 90 to 100% of the pit cavity.
*Eating quality.*—Best, very good flavor with medium acidity and sweetness.

Stone:
*Size.*—Length 40 mm, width 30 mm, thickness 18 mm.
*Form.*—Ovate.
*Apex.*—Pointed, very wide.
*Sides.*—Nearly equal.
*Base.*—Straight.
*Surface.*—Pitted to furrowed throughout.
*Color.*—Grayed orange 175 A.
*Type.*—*Freestone.*
*Tendency to crack.*—None.

Use: Desert, fresh and commercial market.
Shipping quality: Excellent.
Keeping quality: Excellent, will hold for 4 weeks in common cold storage. Disease resistance: good resistance to bacterial spot.

We claim:

1. A new and distinct variety of peach tree, *Prunus persica*, substantially as herein shown and described, characterized particularly as to novelty by the unique combination of vigorous, medium density, regular bearing tree, with resistance to bacterial spot producing freestone fruits having clear yellow, non-browning flesh and substantially round, firm, 80 to 90% dark-red, blush skin color at maturity which occurs 30 days after 'Redhaven' peach.

* * * * *

FA 17